United States Patent
Muse et al.

(10) Patent No.: US 12,260,356 B2
(45) Date of Patent: Mar. 25, 2025

(54) MACHINE LEARNING TECHNIQUES FOR OPTIMIZED EQUIPMENT ALLOCATION

(71) Applicant: UnitedHealth Group Incorporated, Minnetonka, MN (US)

(72) Inventors: Jon Kevin Muse, Thompsons Station, TN (US); Gregory J. Boss, Saginaw, MI (US); Rama S. Ravindranathan, Edison, NJ (US); Marilyn L. Gordon, Cherry Hill, NJ (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 247 days.

(21) Appl. No.: 17/470,551

(22) Filed: Sep. 9, 2021

(65) Prior Publication Data

US 2023/0073776 A1    Mar. 9, 2023

(51) Int. Cl.
| | |
|---|---|
| G06Q 10/0631 | (2023.01) |
| G06Q 10/0635 | (2023.01) |
| G16H 40/20 | (2018.01) |
| G16H 40/40 | (2018.01) |
| G16H 50/30 | (2018.01) |
| G16H 50/80 | (2018.01) |

(52) U.S. Cl.
CPC ..... *G06Q 10/0631* (2013.01); *G06Q 10/0635* (2013.01); *G16H 40/20* (2018.01); *G16H 40/40* (2018.01); *G16H 50/30* (2018.01); *G16H 50/80* (2018.01)

(58) Field of Classification Search
CPC ........ G16H 50/80; G16H 40/40; G16H 40/20; G16H 50/30; G06Q 10/0631; G06Q 10/0635

USPC .......................................................... 705/7.12
See application file for complete search history.

(56) References Cited

U.S. PATENT DOCUMENTS

| | | |
|---|---|---|
| 7,362,228 B2 | 4/2008 | Nycz et al. |
| 7,817,046 B2 | 10/2010 | Coveley et al. |
| 7,837,694 B2 | 11/2010 | Tethrake et al. |
| 9,433,474 B2 | 9/2016 | Swinney |
| 9,741,233 B2 | 8/2017 | Laufer et al. |
| 9,956,306 B2 | 5/2018 | Brais et al. |
| 10,255,466 B2 | 4/2019 | Jinadatha |
| 10,803,993 B2 | 10/2020 | Huang |
| 2008/0208750 A1 | 8/2008 | Chen |
| 2020/0364884 A1 | 11/2020 | Trim et al. |

(Continued)

OTHER PUBLICATIONS

"Hospital RFID Inventory Management of Medical Supplies," Terso Solutions, Inc., (online), [Retrieved from the Internet Nov. 23, 2021]<URL: https://www.tersosolutions.com/hospital-rfid-inventory-management/?gclid=EAlalQobChMIIKeL7Mzy6g/VQdbACh0_RgUuEAAYASAAEglF1vD_BwE>.

(Continued)

Primary Examiner — Charles Guiliano
(74) Attorney, Agent, or Firm — Alston & Bird LLP

(57) ABSTRACT

Various embodiments of the present invention provide methods, apparatus, systems, computing devices, computing entities, and/or the like for performing optimized equipment allocation. Certain embodiments of the present invention utilize systems, methods, and computer program products that perform optimized equipment allocation using at least one of equipment evaluation scoring machine learning models, equipment optimized allocation machine learning models, and equipment history events.

20 Claims, 7 Drawing Sheets

(56) References Cited

U.S. PATENT DOCUMENTS

| | | | | |
|---|---|---|---|---|
| 2021/0073449 | A1* | 3/2021 | Segev | G06F 30/27 |
| 2021/0313075 | A1* | 10/2021 | Mc Namara | G08B 21/22 |
| 2023/0120290 | A1* | 4/2023 | Baarman | G16H 10/65 |
| | | | | 15/3 |

OTHER PUBLICATIONS

"Medical Device Contamination," ScienceDirect, (3 pages), available online at https://www.sciencedirect.com/topics/medicine-and-dentistry/medical-device-contamination/pdf.

Merkel, Matthias Johannes et al. "Statewide Real-Time Tracking of Beds and Ventilators During Coronavirus Disease 2019 and Beyond," Critical Care Explorations, vol. 2, Issue 6: p3e0142, Jun. 2020, DOI: 10.1097/CCE.0000000000000142.

Pennic, Fred. "COVID-19: National Medical Device Registry Launches to Track Ventilators for Hospitals," HIT Consultant, Apr. 17, 2020, (11 pages), (article, online), [Retrieved from the Internet Nov. 23, 2021] <URL: https://hitconsultant.net/2020/04/17/locatorx-launches-national-medical-device-registry-to-track-ventilators-for-hospitals/#YZ1M6tDMKUI>.

Rodrigues, Dayane Otero et al. "Epidemiology of Bacterial Contamination of Inert Hospital Surfaces and Equipment In Critical and Non-Critical Care Units: a Brazilian Study," Microbiology Research Journal International, vol. 30, No. 7, Article No. MRJI.59395, Aug. 6, 2020, pp. 31-43, ISSN: 2456-7043, available online at https://www.journalmrji.com/index.php/MRJI/article/view/30237/56734.

Sahiledengle, Biniyam. "Decontamination of Patient Equipment—Nurses' Self-Reported Decontamination Practice in Hospitals of Southeast Ethiopia," BMC Research Notes, vol. 12, No. 392, Jul. 12, 2019, pp. 1-7, DOI: 10.1186/s13104-019-4427-5.

Stubblefield, Heaven. "What Are Nosocomial Infections?" Healthline, Jun. 6, 2017, (10 pages), (article, online), [Retrieved from the Internet Nov. 23, 2021] <URL: https://www.healthline.com/health/hospital-acquired-nosocomial-infections>.

Trivedi, Amee et al. "WiFiTrace: Network-Based Contact Tracing for Infectious Diseases Using Passive WiFi Sensing," Proceedings of the ACM On Interactive, Mobile, Wearable and Ubiquitous Tecnologies, vol. 5, No. 1, Article 37, Mar. 2021, pp. 1-26. (arXiv: 2005.12045v3 [cs.NI] Jan. 29, 2021).

* cited by examiner

ALERT!

Equipment ID 546234

Placed in off-limits area of facility

MACHINE LEARNING TECHNIQUES FOR OPTIMIZED EQUIPMENT ALLOCATION

BACKGROUND

Various embodiments of the present invention address technical challenges related to performing equipment allocation. Various embodiments of the present invention disclose innovative techniques for efficiently and effectively performing optimized equipment allocation using various predictive data analysis techniques.

BRIEF SUMMARY

Various embodiments of the present invention provide methods, apparatus, systems, computing devices, computing entities, and/or the like for performing optimized equipment allocation. Certain embodiments of the present invention utilize systems, methods, and computer program products that perform optimized equipment allocation using at least one of equipment evaluation scoring machine learning models, equipment optimized allocation machine learning models, and equipment history events.

In accordance with one aspect, a method is provided. In one embodiment, the method comprises: identifying a plurality of equipment items; for each equipment item: retrieving one or more equipment history events; and generating, based at least in part on the one or more equipment history events and by utilizing an equipment evaluation scoring machine learning model, a predicted evaluation score set associated with the equipment item, wherein the predicted evaluation score set includes a per-category predicted evaluation score for the equipment item with respect to a risk category of a plurality of risk categories; and generating, based at least in part on each predicted evaluation score set for an equipment item and by utilizing an equipment optimized allocation machine learning model, an optimized allocation scheme for the plurality of equipment items with respect to the plurality of demand points; and performing, using the one or more processors, one or more prediction-based actions based at least in part on the optimized allocation scheme.

In accordance with another aspect, a computer program product is provided. The computer program product may comprise at least one computer-readable storage medium having computer-readable program code portions stored therein, the computer-readable program code portions comprising executable portions configured to: identify a plurality of equipment items; for each equipment item: retrieve one or more equipment history events; and generate, based at least in part on the one or more equipment history events, and by utilizing an equipment evaluation scoring machine learning model, a predicted evaluation score set associated with the equipment item, wherein the predicted evaluation score set includes a per-category predicted evaluation score for the equipment item with respect to a risk category of a plurality of risk categories; and generate, based at least in part on each predicted evaluation score set for an equipment item, and by utilizing an equipment optimized allocation machine learning model, an optimized allocation scheme for the plurality of equipment items with respect to the plurality of demand points; and perform one or more prediction-based actions based at least in part on the optimized allocation scheme.

In accordance with yet another aspect, an apparatus comprising at least one processor and at least one memory including computer program code is provided. In one embodiment, the at least one memory and the computer program code may be configured to, with the processor, cause the apparatus to: identify a plurality of equipment items; for each equipment item: retrieve one or more equipment history events; and generate, based at least in part on the one or more equipment history events, and by utilizing an equipment evaluation scoring machine learning model, a predicted evaluation score set associated with the equipment item, wherein the predicted evaluation score set includes a per-category predicted evaluation score for the equipment item with respect to a risk category of a plurality of risk categories; and generate, based at least in part on each predicted evaluation score set for an equipment item, and by utilizing an equipment optimized allocation machine learning model, an optimized allocation scheme for the plurality of equipment items with respect to the plurality of demand points; and perform one or more prediction-based actions based at least in part on the optimized allocation scheme.

BRIEF DESCRIPTION OF THE DRAWINGS

Figure 1:
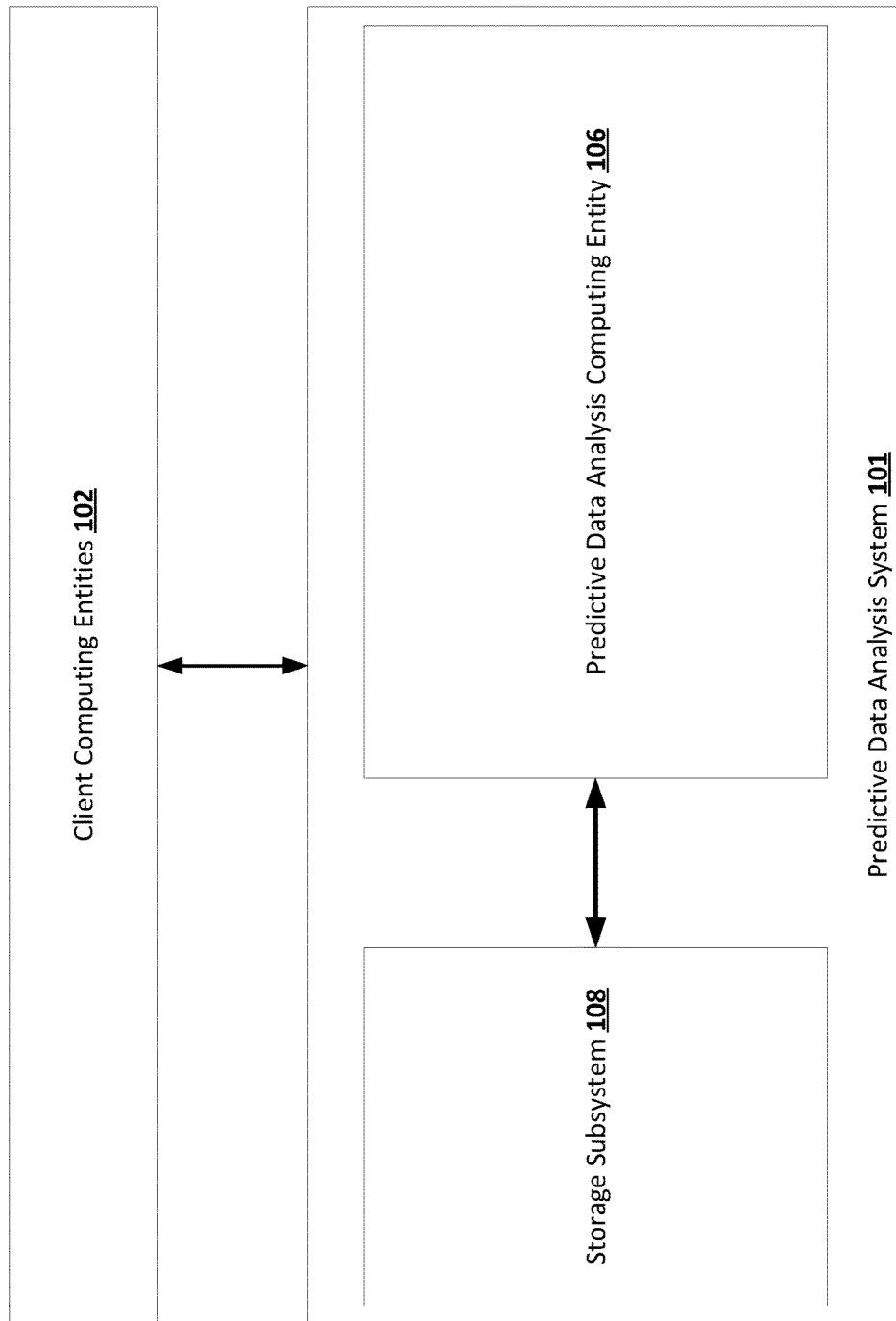

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
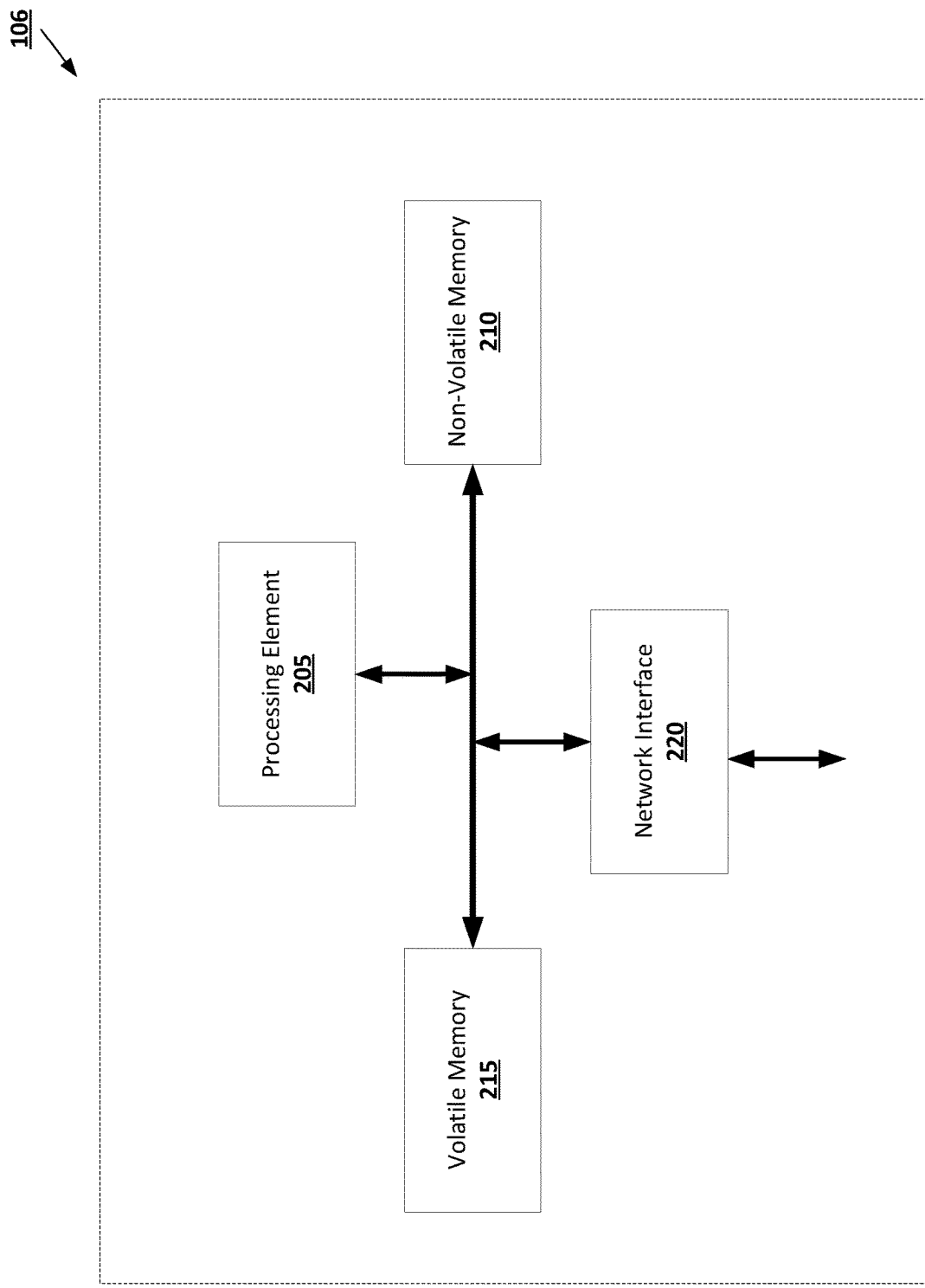

FIG. 2 provides an example predictive data analysis computing entity in accordance with some embodiments discussed herein.

Figure 3:
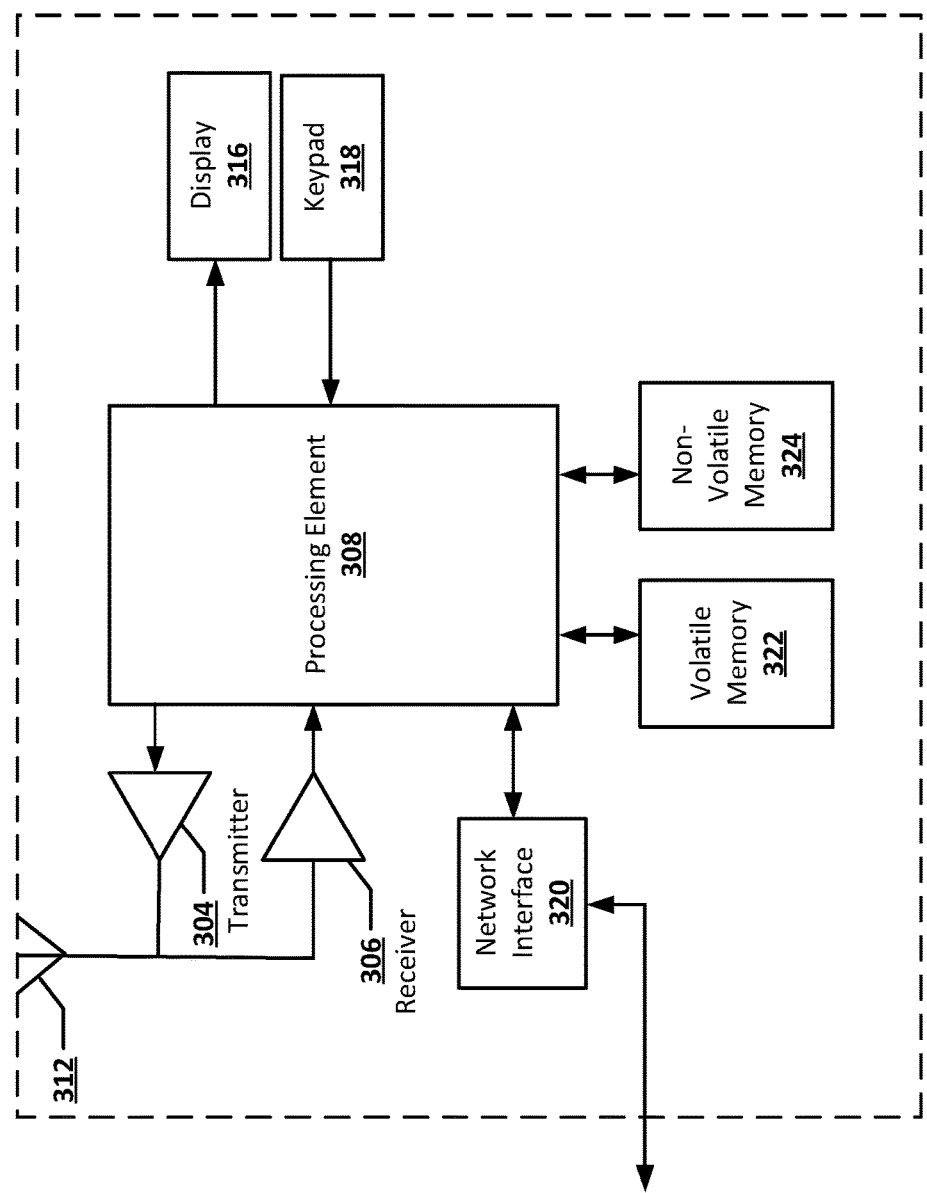

FIG. 3 provides an example client computing entity in accordance with some embodiments discussed herein.

Figure 4:
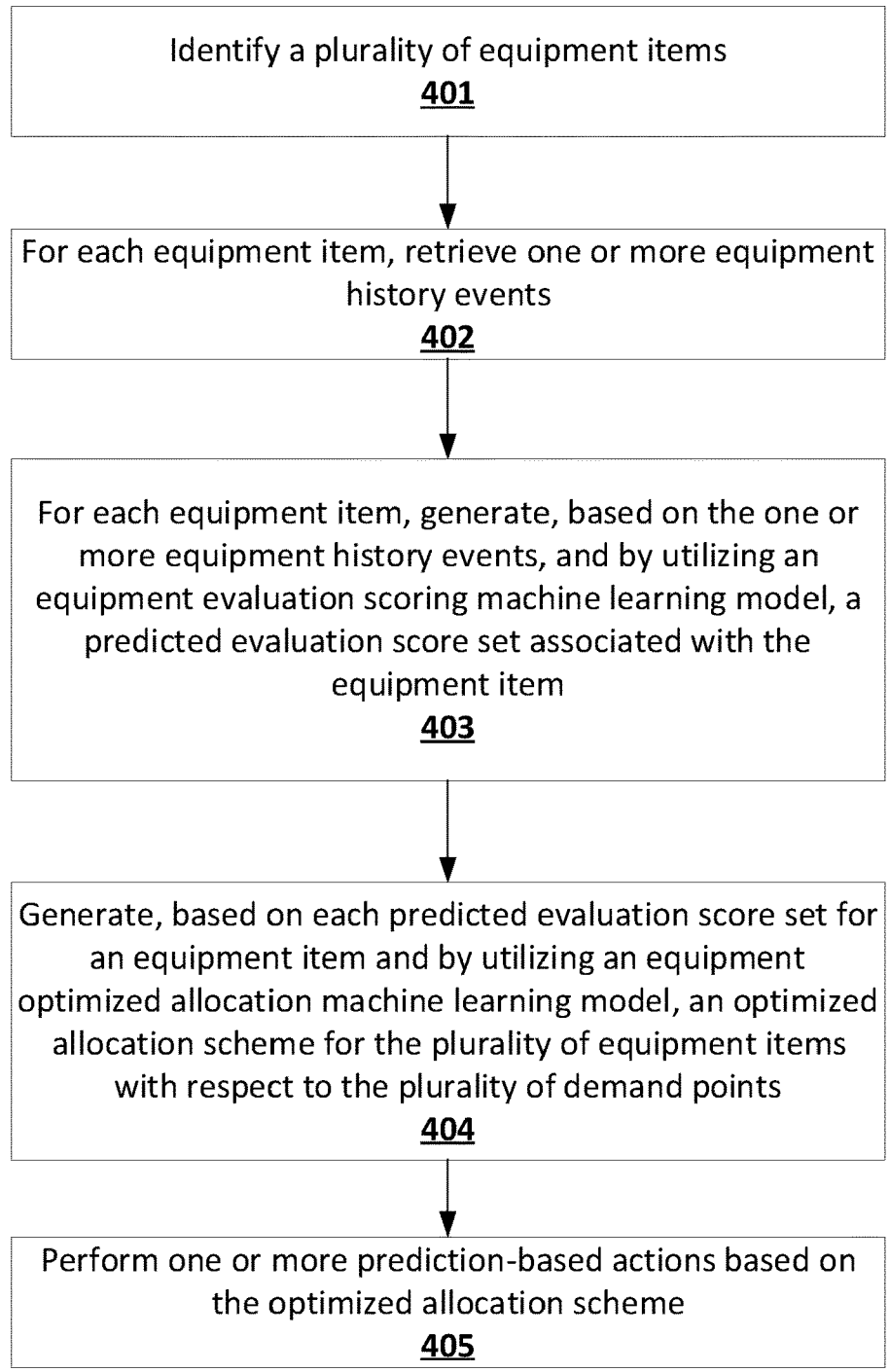

FIG. 4 is a flowchart diagram of an example process for optimized equipment allocation in accordance with some embodiments discussed herein.

Figure 5:

FIG. 5 provides an example user interface depicting one or more notifications, in accordance with some embodiments, discussed herein.

Figure 6:
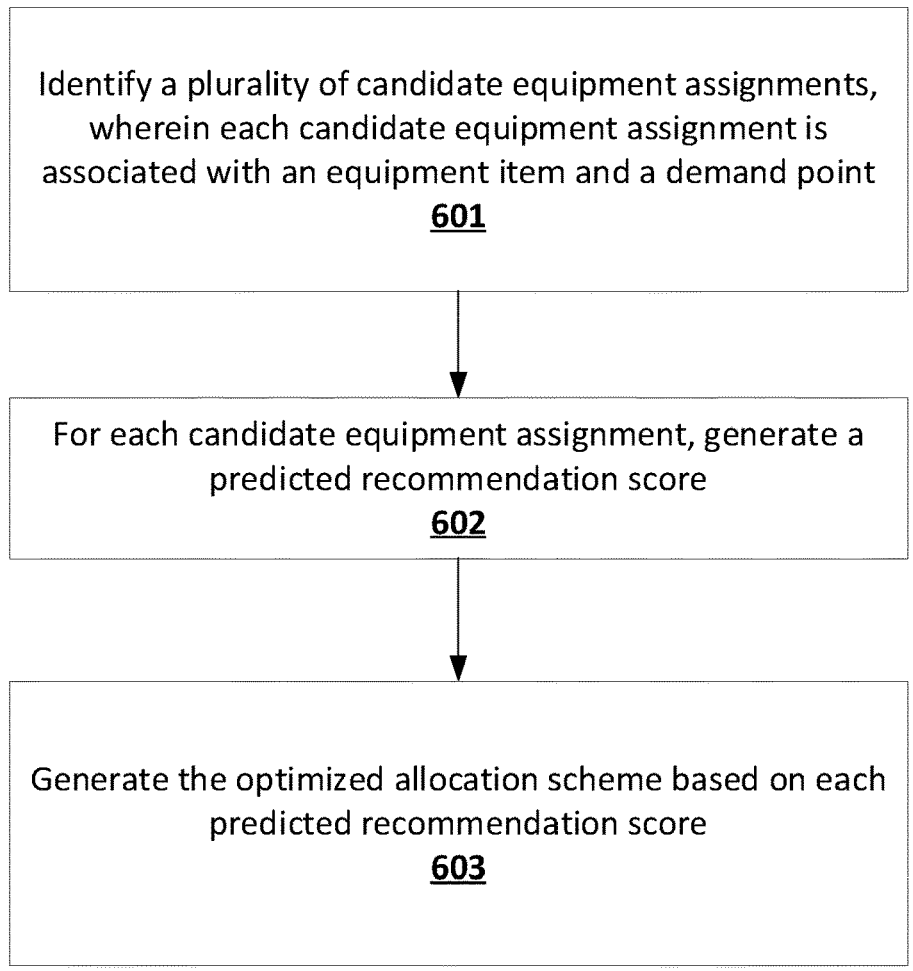

FIG. 6 is a flowchart diagram of an example process for generating an optimized allocation scheme utilizing an equipment optimized allocation machine learning model in accordance with some embodiments discussed herein.

Figure 7:
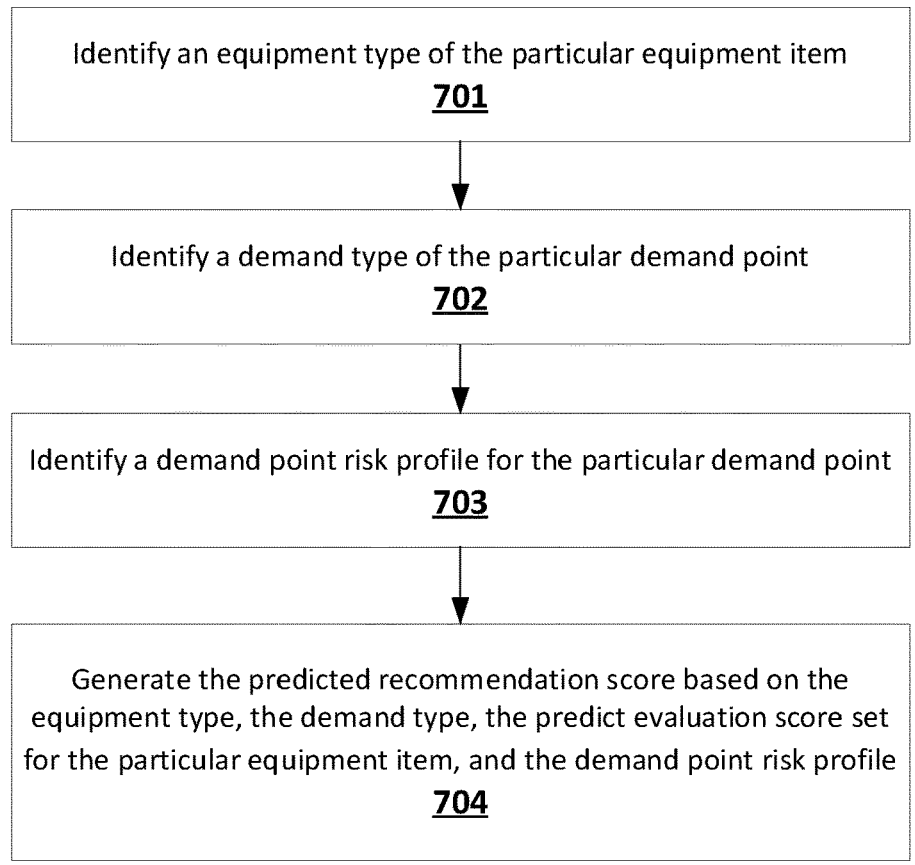

FIG. 7 is a flowchart diagram of an example process for generating a predicted recommendation score for a particular equipment assignment that is associated with a particular equipment item and a particular demand point in accordance with some embodiments discussed herein.

DETAILED DESCRIPTION

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW AND TECHNICAL IMPROVEMENTS

Various embodiments of the present invention address technical challenges related to efficiently and effectively performing optimized equipment allocation across a plurality of demand points based at least in part on one or more equipment history events associated with an equipment item. The disclosed techniques improve the efficiency and effectiveness of optimized equipment allocation by utilizing an equipment evaluation scoring machine learning model that is configured to generate a predicted evaluation score set based at least in part on one or more equipment history events and an equipment optimized allocation machine learning model configured to generate an optimized allocation scheme based at least in part on the predicted evaluation score set.

The equipment evaluation scoring machine learning models and equipment optimized allocation machine learning models utilize operations that may, in at least some embodiments, reduce or eliminate the need for computationally expensive training operations in order to generate the noted equipment evaluation scoring machine learning models and equipment optimized allocation machine learning models. By reducing or eliminating the noted training operations, various embodiments of the present invention: (i) reduce or eliminate the computational operations needed for training and thus improves the computational efficiency of performing optimized equipment allocation, (ii) reduce or eliminate the need for storage resources to train/generate equipment evaluation scoring machine learning models and equipment optimized allocation machine learning models and thus improves storage efficiency of performing optimized equipment allocation, and (iii) reduces or eliminates the need for transmitting extensive training data needed to generate equipment evaluation scoring machine learning models and equipment optimized allocation machine learning models and thus improves transmission/network efficiency of performing optimal equipment allocation. Via the noted advantages, various embodiments of the present invention make substantial technical contributions to the fields of equipment allocation in particular and healthcare-related predictive data analysis in general.

An exemplary application of various embodiments of the present invention relates to proactively optimizing allocation of equipment items to patients at a medical facility to reduce patient infection risk. There is a serious risk of transferring disease from patient to equipment and then from equipment to new patient or supporting medical personnel in addition to re-use of accessories with different equipment items. Cleaning equipment thoroughly relies heavily on the ability of maintenance personnel. Optimizing allocation of equipment items to patients may help prevent contamination risk to patients due to improper day-to-day maintenance, equipment placement or non-adherence to manufacturer requirements.

II. DEFINITIONS

The term "location data object" may refer to an electronically-stored data construct that is configured to describe a measure of location of placement of a corresponding presence-detecting sensor device relative to one or more other location data objects associated with one or more other presence-detecting sensor devices. For example, a particular location data object may describe the measure of location of placement of a Wi-Fi device. As another example, a particular location data object may describe the measure of location of placement of a badge reader device. As yet another example, a particular location data object may describe the measure of location of placement of a Bluetooth sensor device. As a further example, a particular location data object may describe the measure of location of placement of a camera device. As yet further example, a particular location data object may describe the measure of location of placement of a mobile phone (e.g., mobile phone of physicians, nurses, aids, clinicians, and/or the like). Examples of location measures described by location data object include absolute location measures (e.g., absolute location measures described in accordance with the Global Positioning System (GPS)) as well as relative location measures (e.g., relative location measures that describe the location of a particular presence-detecting sensor device with respect to the locations of one or more other presence-detecting sensor devices). The location data object may be a one-dimensional array or a two-dimensional array.

The term "presence-detecting sensor device" may refer to an electronically-stored data construct that is configured to describe an electronic device that is configured to detect the presence of an end-user and/or the presence of an end-user device within a locational proximity of the presence-detecting sensor device. Examples of presence-detecting sensor devices include Wi-Fi devices, badge reader devices, Bluetooth sensor devices, camera devices, voice detection devices, mobile phones, and/or the like. As described above, presence-detecting sensor devices may be configured to generate location data objects. In some embodiments, when combined, location data objects may be used to generate a traversal network.

The term "traversal network" may refer to an electronically-stored data construct that is configured to describe one or more locations described by one or more location data objects as well as detected/assumed/given paths between pairs of the noted locations. The traversal network may, in some embodiments, be a graph data object that describes the locations as tracked location nodes and paths between pairs of locations as traversal edges. Because locations described by a traversal network are determined based at least in part on locational information provided by location data objects, and because location data objects are generated by presence-detecting sensor devices, the tracked location nodes of the traversal network describing the locations are in turn associated with the presence-detecting sensor devices, such that every tracked location node describes a location of a monitored environment/facility, where presence of end-users and/or end-user devices within a positional proximity of the noted monitored environment/facility is being monitored by a respective presence-detecting sensor device. The traversal network may be represented as a two-dimensional array.

The term "equipment item" may refer to an electronically-stored data construct that is configured to describe a designated piece of equipment. For example, an equipment item may describe equipment (e.g., ventilator, blood pressure cuff, tonometer, IV catheter, ultrasound machine, stethoscope, pulse oximeter, patient bed, operating room bed, and/or the like) utilized in a medical facility. An equipment item may be assigned to a demand point. For example, a ventilator may be assigned to a patient during the course of treatment of the patient. In some embodiments an equipment item may be associated with one more equipment history events.

The term "equipment evaluation scoring machine learning model" may refer to a data object that is configured to describe parameters, hyper-parameters, and/or defined operations of a model that is configured to generate a predicted evaluation score set for an equipment item in relation to one or more risk categories based at least in part on one or more equipment history events. In some embodiments, the predicted evaluation scoring machine learning model defines a configurable weight for each equipment history event of the one or more equipment history events. In some embodiments, the predicted evaluation score set may include a per-category predicted evaluation score for the equipment item with respect to a risk category of a plurality of risk categories. In some embodiments, the equipment evaluation scoring machine learning model is configured to generate a predicted evaluation score set for an equipment item in relation to one or more risk categories based at least in part on exposure of the equipment item to a contagion point. In some embodiments the equipment evaluation scoring machine learning model may include a storage location event weight for one or more storage location events, a patient exposure event weight for one or more patient exposure events, an equipment service event weight for one or more equipment service events, a handling exposure event weight for one or more handling exposure events, an equipment environment event weight for one or more equipment environment events, and/or an accessory condition event weight for the one or more accessory condition events. In some embodiments, the equipment evaluation scoring machine learning model may comprise a per-category evaluation score equation for a given risk category of the plurality of risk categories. In some embodiments, the predicted evaluation scoring machine learning model is a supervised machine learning model (e.g., a neural network model) trained using label data, where the supervised machine learning model is configured to generate a predicted evaluation score set for each candidate prediction-based action of one or more candidate prediction-based actions and use each predicted interruption score for a candidate prediction-based action to determine the recommended prediction-based actions. In some embodiments, the equipment evaluation scoring machine learning model is an unsupervised machine learning model (e.g., a clustering model).

The term "predicted evaluation score set" may refer to an electronically-stored data construct that is configured to describe a subset of per-category predicted evaluation scores for an equipment item with respect to a risk category. The predicted evaluation score set may be generated based at least in part on one or more equipment history events utilizing an equipment evaluation scoring machine learning model. In some embodiments, the predicted evaluation score set may be configured to be transferred as input to an equipment optimized allocation machine learning model for generating an optimized allocation scheme for a plurality of equipment items with respect to a plurality of demand points.

The term "per category predicted evaluation score" may refer to a data object that is configured to describe a value that in turn describes an inferred risk with respect to a particular risk category that an equipment item may be predicted to have been exposed to one or more contagion points. For example, the per category predicted evaluation score for a particular equipment with respect to a risk category may describe the likelihood that the particular equipment item may transfer disease causing pathogens to another equipment item, patient, healthcare provider, and/or the like. In some embodiments, generating a per-category predicted evaluation score for a particular equipment item and a particular risk category includes generating a contagion proximity score for the particular equipment item with respect to each contagion point of one or more contagion points associated with the particular risk category.

The term "risk category" may refer to an electronically-stored data construct that is configured to describe a health condition category (e.g., a set of one or more related conditions that may be experienced by a set of monitored individuals). For example, a risk category may be characterized by one or more diseases. For example, a particular risk category may be characterized by a particular disease condition. As another example, a particular risk category may be characterized by Measles. As yet another example, a particular risk category may be characterized by influenza. As a further example, a particular risk category may be characterized by influenza and Measles.

The term "equipment optimized allocation machine learning model" may refer to a data object that is configured to describe parameters, hyper-parameters, and/or defined operations of a model that is configured to generate an optimized allocation scheme for a plurality of equipment items with respect to a plurality of demand points based at least in part on each predicted evaluation score set for an equipment item. In some embodiments, generating the optimized allocation scheme using the equipment optimized allocation machine learning model includes identifying a plurality of candidate equipment assignments, where each candidate equipment assignment is associated with an equipment item and a demand point, for each candidate equipment assignment, generating a predicted recommendation score, and generating the optimized allocation scheme based at least in part on each predicted recommendation score. In some embodiments, the equipment optimized allocation machine learning model may comprise an optimized allocation equation. In some embodiments, the equipment optimized allocation machine learning model is a supervised machine learning model (e.g., a neural network model) trained using label data, where the supervised machine learning model is configured to generate an optimized allocation scheme for each candidate prediction-based action of one or more candidate prediction-based actions and use each predicted allocation scheme for a candidate prediction-based action to determine the recommended prediction-based actions. In some embodiments, the equipment optimized allocation machine learning model is an unsupervised machine learning model (e.g., a clustering model). In some embodiments, the inputs to the equipment optimized allocation machine learning model include each predicted evaluation score set for an equipment item, where each predicted evaluation score set may be a vector, and where the combination of the predicted evaluation score sets is a matrix. In some embodiments, the outputs of the equipment optimized allocation machine learning model include an optimized allocation scheme which may be a vector.

The term "machine learning model" may refer to a data object that describes parameters, hyper-parameters, defined operations, and/or defined mappings of a model that is configured to process one or more prediction input values in accordance with one or more trained parameters of the machine learning models in order to generate a prediction. An example of a machine learning model is a mathematically derived algorithm (MDA). An MDA may comprise any algorithm trained using training data to predict one or more outcome variables. Without limitation, an MDA, as used herein, may comprise machine learning frameworks including neural networks, support vector machines, gradient boosts, Markov models, adaptive Bayesian techniques, and statistical models (e.g., timeseries-based forecast models such as autoregressive models, autoregressive moving average models, and/or an autoregressive integrating moving average models). Additionally, and without limitation, an MDA, as used in the singular, may include ensembles using multiple machine learning and/or statistical techniques.

The term "optimized allocation scheme" may refer to an electronically-stored data construct that describes predicted optimal equipment pairing across a plurality of demand points. In some embodiments, the optimized allocation scheme includes, for each demand point of the plurality of demand points, a recommended equipment item of the plurality of equipment items. In some embodiments, an optimized allocation scheme is generated by an equipment optimized allocation machine learning model, which may be configured to generate an optimized allocation scheme for a plurality of equipment items with respect a plurality of demand points based at least in part on each predicted evaluation score set for an equipment item. In some embodiments, generating the optimized allocation scheme using the equipment optimized allocation machine learning model includes identifying a plurality of candidate equipment assignments, where each candidate equipment assignment is associated with an equipment item and a demand point, for each candidate equipment assignment, generating a predicted recommendation score, and generating the optimized allocation scheme based at least in part on each predicted recommendation score. In some embodiments, the equipment optimized allocation machine learning model may comprise an optimized allocation equation.

The term "demand point" may refer to a data object that describes an entity such as a patient with respect to which one or more demands for equipment items may be generated. For example, a demand point may describe an individual visiting a medical facility for diagnosis and/or treatment. In some embodiments, an optimized allocation scheme maps a plurality of equipment items with respect to a plurality of demand points.

The term "facility map" may refer to a data object that describes a physical arrangement of a set of objects that are located in a physical environment (e.g., medical facility). In some embodiments, a facility map may be utilized in generating one or more candidate pathways. In some embodiments, generating an optimal pathway for moving/transporting equipment items to demand points comprises: generating, using the one or more processors, based at least in part on a demand point location of the demand point and an equipment location of the recommended equipment item for the demand point, and by utilizing a facility map associated with the demand point location and the equipment location, a plurality of candidate pathways; for each candidate pathway, determining, using the one or more processors, a pathway exposure risk score based at least in part on any exposure points associated with the candidate pathway; and generating, using the one or more processors, an optimal pathway of the plurality of candidate pathways based at least in part on each pathway exposure risk score.

The term "candidate pathway" may refer to an electronically-stored data construct that is configured to describe a sequence of tracked location nodes in a traversal network along with a timestamp for each tracked location node in the sequence. For example, a candidate pathway may describe a proposed path that an equipment item, a healthcare worker, and/or the like may take to reach a target destination. As another example, a candidate pathway may describe a proposed route for carrying a ventilator to a target destination such as a patient's room, a surgery room, a medical imaging facility room, and/or the like. As previously noted, each tracked location node described by a candidate pathway is associated with a timestamp, where the timestamp may be determined based at least in part on a measure of temporality that is common across all candidate pathways, such that the timestamps can be used to determine encounters with contagion points. In some embodiments, to generate a candidate pathway for an equipment item, a predictive data analysis computing entity identifies a source node within the tracked location nodes of the traversal network that describes a current location of the traversal agent data object, as well as a destination node within the tracked location nodes of the traversal network that describes a destination location of the equipment item. For example, the source node may describe a current location of a ventilator, while the destination node may describe a surgery room to which the ventilator should be transported. In some of the noted embodiments, the predictive data analysis computing entity generates the candidate pathway as a path that connects the source node and the destination node via one or more traversal edges. The candidate pathway may be represented as a linked list of node visitation recommendations.

The term "pathway exposure score" may refer to an electronically-stored data construct that is configured to describe an estimated measure of infectious/contagion exposure risk for a candidate pathway. In some embodiments, generating an optimal pathway for moving/transporting equipment items to demand points comprises: generating, using the one or more processors, based at least in part on a demand point location of the demand point and an equipment location of the recommended equipment item for the demand point, and by utilizing a facility map associated with the demand point location and the equipment location, a plurality of candidate pathways; for each candidate pathway, determining, using the one or more processors, a pathway exposure risk score based at least in part on any exposure points associated with the candidate pathway; and generating, using the one or more processors, an optimal pathway of the plurality of candidate pathways based at least in part on each pathway exposure risk score.

The term "candidate equipment assignment" may refer to an electronically-stored data construct that describes possible pairing of an equipment item with a demand point. In some embodiments, generating an optimized allocation scheme using an equipment optimized allocation machine learning model includes generating for each candidate equipment assignment a predicted recommendation score.

The term "predicted recommendation score" may refer to a data object that is configured to describe a value that in turn describes an inferred equipment assignment recommendation for a demand point. In some embodiments, a predicted recommendation score may be generated for each candidate equipment assignment.

The term "equipment type" may refer to an electronically-stored data construct that describes the type of an equipment item. For example, equipment type may describe a digital wrist blood pressure cuff. As another example, equipment type may describe a mouth thermometer.

The term "demand type" may refer to an electronically-stored data construct that describes one or more attributes associated with a demand point. For example, demand type may describe a medical need and/or equipment need associated with a demand point.

The term "demand point risk profile" may refer to an electronically-stored data construct that describes one or more attributes associated with a demand point. In some embodiments, the demand point risk profile may describe one or more health-related risk factors associated with a demand point. In some embodiments, a demand point risk profile may include age, gender, weight, medical history, comorbidities, pre-existing conditions, and/or the like. In some embodiments, a particular demand point may be assigned a weight value based at least in part on the demand point risk profile.

The term "equipment history event" may refer to a data object that describes attributes (e.g., location, maintenance, handling, duration, frequency within a time period, and/or the like) associated with the movement of an equipment item over a period of time, where a corresponding timestamp may be associated with an equipment history event. Examples of equipment history events include one or more storage location events, one or more patient exposure events, one or more equipment service events, one or more handling exposure events, one or more equipment environment events, and/or one or more accessory condition events. In some embodiments, the equipment evaluation scoring machine learning model comprises a storage location event weight for the one or more storage location events, a patient exposure event weight for the one or more patient exposure events, an equipment service event weight for the one or more equipment service events, a handling exposure event weight for the one or more handling exposure events, an equipment environment event weight for the one or more equipment environment events, and an accessory condition event weight for the one or more accessory condition events.

The term "storage location event" may refer to a data object that describes a recorded equipment history event for a particular equipment item related to storage of the equipment item in one or more locations. For example, a storage location event may describe one or more locations where an equipment item was stored over a period of time. As another example, a storage location event may describe co-location of equipment items. A storage location event may be associated with a timestamp.

The term "patient exposure event" may refer to a data object that describes a recorded equipment history event for a particular equipment item related to exposure of an equipment to a patient. For example, a patient exposure event may describe an occurrence of exposure of an equipment to a patient known to be associated with one or more contagious diseases. As another example, a patient exposure event may describe the condition of the last patient to whom the equipment item was applied. A patient exposure event may be associated with a timestamp.

The term "equipment service event" may refer to a data object that describes a recorded equipment history event for a particular equipment item related to maintenance (e.g., cleaning, decontamination, and/or the like) of the equipment item. For example, an equipment service event may describe the location of an equipment item in a maintenance room for a duration of time. An equipment service event may be associated with a timestamp.

The term "handling exposure event" may refer to a data object that describes a recorded equipment history event for a particular equipment item related to handling of the equipment. For example, a handling exposure event for a particular equipment item may describe an occurrence of handling of the equipment item by a healthcare worker suspected of an infection. A handling exposure event may be associated with a timestamp.

The term "equipment environment event" may refer to a data object that describes a recorded equipment history event for a particular equipment item related to one or more environmental conditions (e.g., room temperature) associated with the equipment item. For example, an equipment environment event for a particular equipment item may describe the location of the equipment item in room with a temperature of 80° F. for one hour. A patient environment exposure event may be associated with a timestamp.

The term "accessory condition event" may refer to a data object that describes a recorded equipment history event for a particular equipment item related to an accessory condition and/or cleaning status associated with the equipment item. An accessory condition event may be associated with a timestamp.

The term "per-category event weight value" may refer to a data object that describes an estimated significance of a corresponding equipment history event for determining a per-category predicted evaluation score for a corresponding equipment item with respect to a risk category. For example, a patient exposure event for the equipment item may be deemed more pertinent for a first target disease/condition (e.g., tuberculosis) relative to a second target disease/condition (e.g., hepatitis). In the noted example, the per-category event weight value for the patient exposure event relative to the first target disease/condition will likely be higher than the per-category event weight for the patient exposure event relative to the second target disease/condition. As another example, a handling exposure event for the equipment item may be deemed more pertinent for a first target disease/condition (e.g., acquired immunodeficiency syndrome (AIDS)) relative to a second target disease/condition (e.g., Flu). In the noted example, the per-category event weight value for the handling exposure event relative to the first target disease/condition will likely be higher than the per-category event weight for the handling exposure event relative to the second target disease/condition. As yet another example, a storage location event for the equipment item may be deemed more pertinent for a particular target disease/condition (e.g., influenza) relative to an accessory condition event for the equipment item. In the noted example, the per-category event weight value for the storage location event for the particular target disease/condition is likely to be higher than the per-category event weight for the accessory condition event for the equipment item.

The term "storage location event weight" may refer to a data object that describes a per-category event weight associated with storage location events of an equipment item. For example, a storage location event for the equipment item may be deemed more pertinent for a first target disease/condition (e.g., tuberculosis) relative to a second target disease/condition (e.g., hepatitis). In the noted example, the per-category event weight value for the storage location event relative to the first target disease/condition will likely be higher than the per-category event weight for the patient exposure event relative to the second target disease/condition. In some embodiments, the storage location event weight is 0.10.

The term "patient exposure event weight" may refer to a data object that describes a per-category event weight associated with patient exposure events of an equipment item. In some embodiments, each one or more equipment history events for an equipment item are determined based at least in part on one or more movement events associated with the equipment item. In some embodiments, the one or more equipment history events for a particular equipment item comprises: one or more storage location events, one or more patient exposure events, one or more equipment service events, one or more handling exposure events, one or more equipment environment events, and one or more accessory condition events. In some embodiments, the patient exposure event weight is 0.25.

The term "equipment service event weight" may refer to a data object that describes a per-category event weight associated with handling exposure events of an equipment item. In some embodiments, each one or more equipment history events for an equipment item are determined based at least in part on one or more movement events associated with the equipment item. In some embodiments, the one or more equipment history events for a particular equipment item comprises: one or more storage location events, one or more patient exposure events, one or more equipment service events, one or more handling exposure events, one or more equipment environment events, and one or more accessory condition events. In some embodiments, the equipment service event weight is 0.15.

The term "handling exposure event weight" may refer to a data object that describes a per-category event weight associated with equipment service events of an equipment item. In some embodiments, each one or more equipment history events for an equipment item are determined based at least in part on one or more movement events associated with the equipment item. In some embodiments, the one or more equipment history events for a particular equipment item comprises: one or more storage location events, one or more patient exposure events, one or more equipment service events, one or more handling exposure events, one or more equipment environment events, and one or more accessory condition events. In some embodiments, the handling exposure event weight is 0.10.

The term "equipment service event weight" may refer to a data object that describes a per-category event weight associated with equipment service events of an equipment item. In some embodiments, each one or more equipment history events for an equipment item are determined based at least in part on one or more movement events associated with the equipment item. In some embodiments, the one or more equipment history events for a particular equipment item comprises: one or more storage location events, one or more patient exposure events, one or more equipment service events, one or more handling exposure events, one or more equipment environment events, and one or more accessory condition events. In some embodiments, the equipment service event weight is 0.20.

The term "accessory condition event weight" may refer to a data object that describes a per-category event weight associated with an accessory condition event of an equipment item. In some embodiments, each one or more equipment history events for an equipment item are determined based at least in part on one or more movement events associated with the equipment item. In some embodiments, the one or more equipment history events for a particular equipment item comprises: one or more storage location events, one or more patient exposure events, one or more equipment service events, one or more handling exposure events, one or more equipment environment events, and one or more accessory condition events. In some embodiments, the accessory condition event weight is 0.20.

The term "contagion proximity score" may refer to a data object that is configured to describe a value that in turn describes an inferred proximity of an equipment item to a contagion point of one or more contagion points associated with a particular risk category. A contagion proximity score may be determined based at least in part on one or more equipment history events utilizing an equipment scoring machine learning model. In some embodiments, the contagion proximity score may be configured to be transferred as input to an equipment optimized allocation machine learning model for generating an optimized allocation scheme for a plurality of equipment items with respect to a plurality of demand points.

The term "contagion point" may refer to an electronically-stored data construct that describes a source of contagion exposure of an equipment item. Examples of contagion points may include, patients, nurses, staff, doctors, and/or the like with known or suspected infections, equipment items with a high per-category evaluation score with respect to a particular risk category, surfaces with known exposure to contagion points, and/or proximity to any contagious sources.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like, executing instructions stored on a computer-readable storage medium to perform certain steps or operations. Thus, embodiments of the present invention may also take the form of an entirely hardware embodiment, an entirely computer program product embodiment, and/or an embodiment that comprises a combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example architecture 100 for performing predictive data analysis. The architecture 100 includes a predictive data analysis system 101 configured to generate predictive outputs that lead to performing one or more prediction. In some embodiments, the predictive data analysis system 101 may be configured to receive predictive data analysis requests from client computing entities 102, process the predictive data analysis requests to generate predictions, provide the generated predictions to the client computing entities 102, and automatically perform prediction-based actions based at least in part on the generated predictions.

An example of a prediction-based action that can be performed using the predictive data analysis system 101 is a request for generating a predicted evaluation score set for a plurality of equipment items corresponding to predicted exposure of the equipment to one or more infections and/or pathogens and optimizing equipment allocation across a plurality of demand points corresponding to optimal pairing of an equipment to a patient. Prediction of the potential exposure of an equipment item to pathogens and/or optimizing equipment allocation plays an important role in medical and insurance fields. For example, it reduces the risk of transferring a disease from a patient to an equipment item and then from the equipment item to another patient, a physician, a healthcare worker, and/or the like.

In some embodiments, predictive data analysis system 101 may communicate with at least one of the client computing entities 102 using one or more communication networks. Examples of communication networks include any wired or wireless communication networks including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more client computing entities 102, process the predictive data analysis requests to generate predictions corresponding to the predictive data analysis requests, provide the generated predictions to the client computing entities 102, and automatically perform prediction-based actions based at least in part on the generated predictions.

The storage subsystem 108 may be configured to store input data used by the predictive data analysis computing entity 106 to perform predictive data analysis, as well as model definition data used by the predictive data analysis computing entity 106 to perform various predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein, interchangeably. In one embodiment, these functions, operations, and/or processes can be performed on data, content, information, and/or similar terms used herein, interchangeably.

As indicated, in one embodiment, the predictive data analysis computing entity 106 may also include one or more network interfaces 220 for communicating with various computing entities, such as by communicating data, content, information, and/or similar terms used herein, interchangeably, that can be transmitted, received, operated on, processed, displayed, stored, and/or the like.

As shown in FIG. 2, in one embodiment, the predictive data analysis computing entity 106 may include, or be in communication with, one or more processing elements 205 (also referred to as processors, processing circuitry, and/or similar terms used herein, interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include, or be in communication with, non-volatile media (also referred to as non-volatile storage, memory, memory storage, memory circuitry and/or similar terms used herein, interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein, interchangeably, may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include, or be in communication with, volatile media (also referred to as volatile storage, memory, memory storage, memory circuitry and/or similar terms used herein, interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more network interfaces 220 for communicating with various computing entities, such as by communicating data, content, information, and/or similar terms used herein, interchangeably, that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

Exemplary Client Computing Entity

FIG. 3 provides an illustrative schematic representative of a client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the predictive data analysis computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the predictive data analysis computing entity 106 via a network interface 320.

Via these communication standards and protocols, the client computing entity 102 can communicate with various other entities using concepts, such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein, interchangeably, executing on and/or accessible via the client computing entity 102 to interact with and/or cause display of information/data from the predictive data analysis computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the predictive data analysis computing entity 106 and/or various other computing entities.

In another embodiment, the client computing entity 102 may include one or more components or functionalities that are the same or similar to those of the predictive data analysis computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

Exemplary System Operations

As described below, various embodiments of the present invention address technical challenges related to efficiently and effectively performing optimized equipment allocation across a plurality of demand points based at least in part on one or more equipment history events associated with an equipment item. The disclosed techniques improve the efficiency and effectiveness of optimized equipment allocation by utilizing an equipment evaluation scoring machine learning model that is configured to generate a predicted evaluation score set based at least in part on one or more equipment history events and an equipment optimized allocation machine learning model configured to generate an optimized allocation scheme based at least in part on the predicted evaluation score set.

Various embodiments of the present invention provide techniques for efficiently optimizing the allocation of an equipment item by performing inferences about the equipment item events. FIG. 4 is a flowchart diagram of an example process 400 for optimized equipment allocation across a plurality of demand points. While various embodiments of the present invention may describe performing multiple techniques using a singular computing entity, a person of ordinary skill in the relevant technology will recognize that each of the disclosed techniques can be performed by a separate computing entity. The process 400 will now be described with reference to the predictive data analysis computing entity 106 of the predictive data analysis system 101, as described above in relation to FIG. 1.

The process 400 begins at step/operation 401 when the predictive data analysis computing entity 106 identifies a plurality of equipment items. Examples of equipment items include ventilators, blood pressure cuffs, tonometer, IV catheter, ultrasound machine, stethoscope, pulse oximeter, patient bed, operating room bed, and/or the like. For example, a healthcare facility (e.g., a hospital, an immediate care center, and/or the like) may possess one or more equipment items that may be used in the course of treating a particular patient and the one or more equipment items may be re-used in the course of treating another patient. In the noted example, a particular blood pressure cuff may be used to measure the blood pressure of patient A and the particular blood pressure cuff subsequently used to measure the blood pressure of patient B. As another example, a particular ventilator may be used on a patient C infected with influenza and the particular ventilator used on patient D not infected with influenza.

In some embodiments, the predictive data analysis computing entity 106 identifies the plurality of equipment items based at least in part on one or more demand points and/or one or more equipment item profiles. In some embodiments, the predictive data analysis computing entity 106 may store one or more equipment item profiles, where each equipment item profile is associated with a particular equipment item and where each equipment item profile includes a subset of equipment item data that each describe one or more attributes associated with the particular equipment item. For example, an equipment profile may include manufacturing data (e.g., manufacturing date, manufacturing number, and/or the like) associated with an equipment item. As another example, an equipment profile may include data that describes error codes associated with an equipment. As yet another example, an equipment profile may include data that describes equipment logging associated with an equipment profile. As a further example, an equipment profile may include a unique ID associated with a particular equipment. As yet further example, an equipment profile may include data describing the equipment type.

In some embodiments, additionally and/or alternatively, the predictive data analysis computing entity 106 may store one or more patient data profiles, where each patient data profile is associated with a particular patient and where each patient data profile includes a subset of patient data that each describe one or more attributes associated with the particular patient. For example, in some embodiments, the predictive data analysis computing entity 106 may receive, retrieve, and/or store patient data that describes particular patient assignments and/or treatment plan for a particular patient. As another example, in some embodiments, the predictive data analysis computing entity 106 may receive, retrieve, and/or store patient data that describes patient room number, suite, and/or location for a particular patient. As yet another example, in some embodiments, the predictive data analysis computing entity 106 may receive, retrieve, and/or store patient data that describes one or more diseases and/or illnesses associated with a particular patient. As yet further example, in some embodiments, the predictive data analysis computing entity 106 may receive, retrieve, and/or store patient data that describes reported comorbidities associated with a particular patient.

In some embodiments, for each patient, the predictive data analysis computing entity 106 may receive, retrieve, and/or store patient data that describes particular patient assignment and/or treatment plan for the particular patient, patient data that describes patient room number, suite, and/or location for the particular patient, patient data that describes one or more diseases and/or illnesses associated with the particular patient, patient data that describes reported comorbidities associated with the particular patient, and/or the like. In some embodiments, one more of the patient data may be retrieved from an Electronic Medical Record (EMR), where the EMR may be stored on a computing entity.

Additionally and/or alternatively, the predictive data analysis computing entity 106 may receive, retrieve, and/or store personnel data that describes one or more human resources-related information. For example, in some embodiments, the predictive data analysis computing entity 106 may receive, retrieve, and/or store for a medical facility employee information, shift schedule, time clock entries, maintenance personnel on duty, physician on duty, and or the like. In some embodiments, the predictive data analysis computing entity 106 may generate an optimized personnel assignment based at least in part on the human resources-related information such that contagion transfer risk may be reduced.

Additionally and/or alternatively, the predictive data analysis computing entity 106 may store one or more subsets of equipment history events, where each subset of equipment history events is associated with a particular equipment item. In some embodiments, a subset of equipment history events may include one or more storage location events, one or more patient exposure events, one or more equipment service events, one or more handling exposure events, one or more equipment environment events, and/or one or more accessory condition events. In some embodiments the one or more equipment history events for a particular equipment item may be determined based at least in part on one or more movement events associated with the equipment item. For example, in some embodiments, the predictive data analysis may record data (e.g., date, time, location, duration, frequency, and/or the like) associated with one or more movement events associated with a particular equipment item. For example, the predictive data analysis computing entity 106 may record data associated with movement of a particular equipment item pre-delivery to a particular patient, data associated with movement of the particular equipment item during the course of treatment of the particular patient, and/or data associated with movement of the particular equipment item post treatment of the particular patient. As another example, the predictive data analysis computing entity 106 may record data associated with movement of a particular equipment to a storage location and/or out of a storage location. As yet another example, the predictive data analysis computing entity 106 may record data associated with movement of a particular equipment to a maintenance room (e.g., cleaning and/or decontamination room). As further example, the predictive data analysis computing entity 106 may record data associated with movement of a particular equipment to an operating room.

In some embodiments, the predictive data analysis computing entity 106 may determine one or more co-equipment proximity scores for a particular equipment item with respect to one or more other equipment items, where each co-equipment proximity score describes the proximity of the particular equipment item to another given equipment item. In some embodiments, the predictive data analysis computing entity 106 may determine, based at least in part on the one or more co-equipment proximity scores, the storage locations of the particular equipment within a given time period. In some embodiments, the predictive data analysis computing entity 106 may determine, based at least in part on the one or more co-equipment proximity scores, the maintenance history of the particular equipment item. For example, the predictive data analysis computing entity 106 may determine the frequency and/or duration of the particular equipment item at one or more maintenance locations within a given time period based at least in part on one or more co-equipment proximity scores. In some embodiments, the predictive data analysis computing entity 106 may determine, based at least in part on the one or more co-equipment proximity scores, one or more locations (e.g., patient room) associated with the particular equipment item.

In some embodiments, the predictive data analysis computing entity 106 may determine a predicted evaluation score set for a particular equipment item based at least in part on the one or more equipment history events associated with the particular equipment item. In some embodiments determining the one or more equipment history events for the particular equipment based at least in part on one or more movement events associated with the particular equipment item may include receiving one or more location data objects from one more presence detecting sensor devices. For example, the predictive data analysis computing entity 106 may receive location data objects from at least one or one or more Wi-Fi devices, one or more badge reader devices, one or more Bluetooth sensor devices, one or more camera devices, one or more voice detection devices, one or more mobile phones, and/or the like.

In general, a location data object may describe a measure of location of placement of a corresponding presence-detecting sensor device relative to one or more other location data objects associated with one or more other presence-detecting sensor devices. For example, a particular location data object may describe the measure of location of placement of a Wi-Fi device. As another example, a particular location data object may describe the measure of location of placement of a badge reader device. As yet another example, a particular location data object may describe the measure of location of placement of a Bluetooth sensor device. As a further example, a particular location data object may describe the measure of location of placement of a camera device. As yet further example, a particular location data object may describe the measure of location of placement of a mobile phone (e.g., mobile phone of physicians, nurses, aids, clinicians, and/or the like). Examples of location measures described by location data object include absolute location measures (e.g., absolute location measures described in accordance with the Global Positioning System (GPS)) as well as relative location measures (e.g., relative location measures that describe the location of a particular presence-detecting sensor device with respect to the locations of one or more other presence-detecting sensor devices).

A presence-detecting sensor device may describe an electronic device that is configured to detect the presence of an end-user and/or the presence of an end-user device within a locational proximity of the presence-detecting sensor device. For example, in some embodiments, the presence-detecting device may be configured to detect the presence of an equipment item, a physician, a health provider, a patient, a hospital visitor, and/or the like. For example, in some embodiments, one or more presence-detecting sensors may be located on an equipment item. Additionally and/or alternatively, one or more presence detecting sensors may be located on a physician (e.g., on the physician's badge). Additionally and/or alternatively, one or more presence-detecting sensors may be located on a healthcare provider. Additionally and/or alternatively, one or more presence-detecting sensors may be located on a maintenance personnel (e.g., a hospital worker responsible for cleaning one or more equipment items). Additionally and/or alternatively, one or more presence-detecting sensors may be located on a hospital visitor (e.g., on a temporary badge and/or the like). Additionally and/or alternatively, one or more presence-detecting sensors may be located on a patient (e.g., on an ID wrist band, and/or the like). Additionally and/or alternatively, one or more presence-detecting sensors may be located in a patient room. Additionally and/or alternatively, one more presence-detecting sensors may be located in a storage room. Additionally and/or alternatively, one or more presence-detecting sensors may be located in an operating room. Additionally and/or alternatively, one or more presence-detecting sensors may be located in one or more strategic locations and/or the like.

Examples of presence-detecting sensor devices include Wi-Fi devices, badge reader devices, Bluetooth sensor devices (e.g., Bluetooth low Energy (BLE), and/or the like), camera devices, voice detection devices, mobile phones, and/or the like. As described above, presence-detecting sensor devices may be configured to generate location data objects. In some embodiments, when combined, location data objects may be used to generate a traversal network. In some embodiments, the data schema for a location data object may include: (i) a Device ID field that is configured to describe the presence-detecting sensor device that is associated with the location data object, (ii) a Device Type field that is configured to describe a type of the presence-detecting sensor device that is associated with the location data object, (iii) a Device Location field that is configured to describe at least one of the locations of the presence-detecting sensor devices that is associated with the location data object or a location measure generated by the presence-detecting sensor device that is associated with the location data object, (iv) a Creation Timestamp field that is configured to describe a time when the presence-detecting sensor device that is associated with the location data object generated, (v) and a Validity Duration that is configured to describe a time period within which the location measure described by the location data object can be deemed to remain valid.

The process continues at step/operation 402, when for each equipment item of the plurality of equipment items, the predictive data analysis computing entity 106 retrieves one or more equipment history events associated with the equipment item. In some embodiments, the predictive data analysis computing entity 106 may retrieve one or more storage location events associated with the particular equipment item. Additionally and/or alternatively, the predictive data analysis computing entity 106 may retrieve one or more patient exposure events associated with the particular equipment item. Additionally and/or alternatively, the predictive data analysis computing entity 106 may retrieve one or more equipment service events associated with the particular equipment item. Additionally and/or alternatively, the predictive data analysis computing entity 106 may retrieve one or more handling exposure events associated with the particular equipment item. Additionally and/or alternatively, the predictive data analysis computing entity 106 may retrieve one or more equipment environment events associated with the particular equipment item. Additionally and/or alternatively, the predictive data analysis computing entity 106 may retrieve one or more accessory condition events associated with the particular equipment item.

At step/operation 403, for each equipment item of the plurality of equipment items, the predictive data analysis computing entity 106 utilizes an equipment evaluation scoring machine learning model to generate a predicted evaluation score set associated with the equipment item based at least in part on the one or more equipment history events. In some embodiments, the predicted evaluation score set may include a per-category predicted evaluation score for the equipment item with respect to a risk category of a plurality of categories. In some embodiments, a risk category may be characterized by one or more diseases. For example, a particular risk category may be characterized by influenza. As another example, a particular risk category may be characterized by Measles. As yet another example, a particular risk category may be characterized by hepatitis. As a further example, a particular risk category may be characterized by influenza and Measles. A per-category predicted evaluation score generally describes a value that describes an inferred risk with respect to a particular risk category that an equipment item may be predicted to have been exposed to one or more contagion points. In some embodiments, examples of contagion points include, patients, nurses, staff, doctors, and/or the like with known or suspected infections, equipment items with a high per-category evaluation score with respect to a particular risk category, surfaces with known exposure to contagion points, and/or proximity to any contagious sources.

As noted above, the equipment evaluation scoring machine learning model may generate the predicted evaluation score set based at least in part on the one or more equipment history events. In some embodiments, each equipment history event of the plurality of equipment history event may be associated with an inferred weight. In some embodiments, the equipment evaluation scoring machine learning model generates an inferred weight for each equipment history event. For example, in some embodiments, the equipment evaluation scoring machine learning model includes a storage location event weight for the one or more storage location events, a patient exposure event weight for the one or more patient exposure events, an equipment service event weight for the one or more equipment service events, a handling exposure event weight for the one or more handling exposure events, an equipment environment event weight for the one or more equipment environment events, and/or an accessory condition event weight for the one or more accessory condition events. For example, in an embodiment, the storage location event weight may be 10%, the patient exposure event weight may be 25%, the equipment service equipment event weight may be 15%, the handling exposure event weight may be 10%, the equipment environment event weight may be 20%, and the accessory condition event weight may be 20%. In some embodiments, the inferred weights may be configurable.

In some embodiments, generating the per-category predicted evaluation score for a particular equipment item with respect to a particular risk category includes generating a contagion proximity score for the particular equipment with respect to each contagion point of the one or more contagion points associated with a particular risk category and generating the per-category predicted evaluation score based at least in part on each contagion proximity score. In some embodiments, the predictive data analysis computing entity 106 stores each generated contagion proximity score. In some embodiments, the predictive data analysis computing entity 106 generates a contagion proximity score for the particular equipment item with respect to each contagion point for each unit of time (e.g., every 5 minutes, every 10 minutes, every hour, and/or the like). In some embodiments, the unit of time may be configurable.

In some embodiments, the one or more per-category evaluation score of a particular equipment item with respect to a particular risk category may be used to determine the likelihood that the particular equipment item may transfer (directly and/or indirectly) one or more pathogens to another equipment item, physician, patient, healthcare provider and/or the like exposed to the particular equipment item. In some embodiments, the per-category predicted evaluation score may be configured to be transferred as input to an equipment optimized allocation machine learning model for generating an optimized allocation scheme for a plurality of equipment items with respect to a plurality of demand points.

In some embodiments, performing the one or more prediction-based actions comprises determining whether one or more per-category evaluation scores satisfies one or more corresponding per-category evaluation score thresholds associated with one or more corresponding risk categories. In some embodiments, the predictive data analysis computing entity 106 may be configured to generate user interface data for display using a display device of a computing entity (e.g., the client computing entity 102). In some embodiments, in response to determining that one or more per-category evaluation scores satisfies one or more corresponding per-category evaluation score threshold associated with the one or more corresponding risk categories, the predictive data analysis computing entity 106 may generate user interface data for one or more notifications. FIG. 5, provides an example user interface 500 depicting one or more notifications, in accordance with some embodiments, discussed herein. As depicted in FIG. 5, examples of the one or more notifications may include alerts, markers in health records indicating that the particular equipment item was placed in an unsuitable, markers in health records indicating that the particular equipment item was placed in off-limits are of the facility, and/or the like.

Returning to FIG. 4 at step/operation 404, the predictive data analysis computing entity 106 utilizes an equipment optimized allocation machine learning model to generate an optimized allocation scheme for the plurality of equipment items with respect to the plurality of demand points based at least in part on each predicted evaluation score set for an equipment. Generating an optimized allocation scheme may help reduce the risk of infection, as it may help reduce the risk of transferring a disease from a patient to an equipment and then from the equipment to another patient, healthcare worker, and/or the like. In some embodiments, the optimized allocation scheme includes a recommended equipment item of the plurality of equipment items. For example, the predictive data analysis computing entity 106 recommends the assignment of a particular equipment to a particular demand point. In some embodiments, the step/operation 404 may be performed in accordance with the process that is depicted in FIG. 6, which is an example process for generating an optimized allocation scheme utilizing an equipment optimized allocation machine learning model.

The process that is depicted in FIG. 6 begins at step operation 601, when the predictive data analysis computing entity 106 identifies a plurality of candidate equipment assignments, where each candidate equipment assignment is associated with an equipment item and a demand point. For example, the predictive data analysis computing entity 106 may determine possible assignments of one or more equipment items to one or more demand points. For example, the predictive data analysis may determine that equipment item A can be assigned to demand point B and also determine that the equipment item A can be assigned to demand points C and D.

At step/operation 602, for each candidate equipment assignment, the predictive data analysis computing entity 106 generates a predicted recommendation score. In some embodiments, generating the predicted recommendation score for a particular candidate equipment assignment may be performed in accordance with the process that is depicted in FIG. 7, which is an example process for generating a predicted recommendation score for a particular candidate equipment assignment that is associated with a particular equipment item and a particular demand point. The process that is depicted in FIG. 7 begins at stop 701 when the predictive data analysis computing entity 106 identifies an equipment type of the particular equipment item, where an equipment type may describe the type of equipment item. For example, an equipment type may be a digital wrist blood pressure cuff. As another example, an equipment type may be a mouth thermometer.

At step/operation 702, the predictive data analysis computing entity 106 may identify a demand type of the particular demand point, where a demand type may describe one or more attributes associated with a demand point. For example, demand type may describe a medical need and/or equipment need associated with a demand point. At step operation 703, the predictive data analysis computing entity 106 may identify a demand point risk profile for the particular demand point, where the demand point risk profile may describe one or more health-related risk factors and/or attributes associated with the demand point. For example, a demand point risk profile may include age, gender, weight, medical history, comorbidities, pre-existing conditions, demand type, and/or the like associated with the particular demand point. At step/operation 704, the predictive data analysis computing entity 106 may generate the predicted recommendation score based at least in part on the equipment type, the demand type, the predicted evaluation score set for the particular equipment item, and the demand point risk profile. In some embodiments, generating the predicted recommendation score may include assigning a weight value to the particular demand point. In some embodiments, the weight value may be assigned based at least in part on the demand point risk profile for the particular demand point. For example, in some embodiments, the demand point may be assigned a weight value based at least in part on one or more attributes (e.g., age, gender, weight, and/or the like). In some embodiments, the weight value associated with a particular demand point may, at least in part, correspond to the predicted recommendation score. As an example, where a particular disease is known to be more dangerous to older individuals (and/or older patients are more at risk) and where two demand points are each associated with the particular disease, the demand point of the two demand points associated with a higher age value may be assigned a higher weight value corresponding to a higher predicted recommendation score relative to the other demand point. In such example, the equipment assignment recommendation favors the demand point with the higher age value. As another example, where a particular disease is known to be more dangerous to younger individuals (and/or younger individuals are more at risk) and where two demand points are each associated with the particular disease, the demand point of the two demand points associated with a lower age value may be assigned a higher weight value corresponding to a higher predicted recommendation score relative to the other demand point. In such example, the equipment assignment recommendation favors the demand point with the lower age value.

Returning to FIG. 6, at step/operation 603, the predictive data analysis computing entity 106 generates the optimized allocation scheme based at least in part on each predicted recommendation score. For example, of two candidate equipment assignments, the predictive data analysis computing entity 106 may recommend the candidate equipment assignment with the higher predicted recommendation score.

In some embodiments, generating an optimized allocation scheme for the plurality of equipment items with respect to the plurality of demand points based at least in part on the predicted evaluation score set for an equipment item includes evaluating each predicted evaluation score set for an equipment item of the plurality of equipment items. Additionally, in some embodiments, generating the optimized allocation scheme includes assigning an equipment item with a demand point based at least in part on comparing the per-category evaluation score set of the equipment item with the demand point risk profile associated with the demand point. For example, the predictive data analysis computing entity 106 may assign an equipment item to a demand point based at least in part on similarity in exposure scores and/or non-exposure histories. In some embodiments, generating the optimized allocation scheme includes avoiding the assignment of an equipment with a high risk profile to a demand point associated with a high demand point risk profile, where, a high risk profile may describe a subset of predicted evaluation score sets or subsets of per-category evaluation scores for an equipment over a period of time exceeding a given threshold. In some embodiments, a high risk profile may describe an equipment predicted to have a high risk of carrying pathogens.

In some embodiments, optimization of equipment assignment may be based at least in part on the predicted evaluation score set and/or contagion proximity scores, and/or co-equipment proximity scores associated with an equipment item of a plurality of equipment items to reduce contagion risk. In some embodiments, the predictive data analysis computing entity 106 associates an equipment with high risk based at least in part on the frequency of high predicted evaluation score sets associated with the equipment item and/or inadequate maintenance (e.g., inadequate cleaning and/or decontamination) of the equipment item. In some embodiments, the predictive data analysis computing entity 106 may determine that an equipment item requires maintenance based at least in part on the equipment predicted evaluation score set. In some embodiments, the predictive data analysis computing entity 106 may determine optimal equipment maintenance based at least in part on the predictive equipment score set associated with an equipment item.

Returning to FIG. 4, at step/operation 405, the predictive data analysis computing entity 106 performs one or more prediction-based actions based at least in part on the optimized allocation scheme. In some embodiments, performing one or more prediction based actions based at least in part on the optimized allocation scheme includes generating an optimal pathway of a plurality of pathways.

As noted above, the presence-detecting sensor devices may be configured to generate location data objects. In some embodiments, the predictive data analysis computing entity 106 generates a traversal network based at least in part on the location data objects. In some embodiments, the predictive data analysis computing entity 106 combines the locational information inferred based at least on the location data objects to generate the traversal network.

A traversal network may describe one or more locations described by one or more location data objects, as well as detected/assumed/given paths between pairs of the noted locations. The traversal network may, in some embodiments, be a graph data object that describes the locations as tracked location nodes and paths between pairs of locations as traversal edges. Because locations described by a traversal network are determined based at least in part on locational information provided by location data objects, and because location data objects are generated by presence-detecting sensor devices, the tracked location nodes of the traversal network describing the locations are in turn associated with the presence-detecting sensor devices, such that every tracked location node describes a location of a monitored environment/facility, where presence of end-users and/or end-user devices within a positional proximity of the noted monitored environment/facility is being monitored by a respective presence-detecting sensor device.

A candidate pathway may describe a sequence of tracked location nodes in a traversal network along with a timestamp for each tracked location node in the sequence. For example, a candidate pathway may describe a proposed path that an equipment item may take to reach a target destination (e.g., a demand point location). In some embodiments, the predictive data analysis computing entity 106, generates a plurality of candidate pathways based at least in part on a demand point location of the demand point and an equipment location of the recommended equipment item.

In some embodiments, to generate a candidate pathway for an equipment item based at least in part on a demand point location of the demand point and an equipment location of the recommended equipment item, the predictive data analysis computing entity 106 identifies a source node within the tracked location nodes of the traversal network that describes a current location of the equipment item, as well as a destination node within the tracked location nodes of the traversal network that describes a destination location of the equipment item. For example, the source node may describe a current location of a ventilator, while the destination node may describe a patient room to which the ventilator should be transported. In some of the noted embodiments, the predictive data analysis computing entity 106 generates the candidate traversal path as a path that connects the source node and the destination node via one or more traversal edges.

In some embodiments, generating the plurality of candidate pathways based at least in part on the location of the demand point and the equipment location of the recommended equipment item includes using a facility map associated with the demand point location and the equipment location. In some embodiments, for each candidate pathway, the predictive data analysis computing entity 106 determines a pathway exposure risk score based at least in part on any exposure points associated with the candidate pathway. In some embodiments, the predictive data analysis computing entity 106 generates an optimal pathway of the plurality of candidate pathways based at least in part on each pathway exposure risk score. In the noted embodiments, generating an optimal pathway may help reduce contagion exposure risk, which may in turn reduce patient infection risk.

As described above, various embodiments of the present invention address technical challenges related to efficiently and effectively performing optimized equipment allocation across a plurality of demand points based at least in part on one or more equipment history events associated with an equipment item. The disclosed techniques improve the efficiency and effectiveness of optimized equipment allocation by utilizing an equipment evaluation scoring machine learning model that is configured to generate a predicted evaluation score set based at least in part on one or more equipment history events and an equipment optimized allocation machine learning model configured to generate an optimized allocation scheme based at least in part on the predicted evaluation score set.

In some embodiments, the equipment evaluation scoring machine learning models and equipment optimized allocation machine learning models utilize operations that may, in at least some embodiments, reduce or eliminate the need for computationally expensive training operations in order to generate the noted equipment evaluation scoring machine learning models and equipment optimized allocation machine learning models. By reducing or eliminating the noted training operations, various embodiments of the present invention: (i) reduce or eliminate the computational operations needed for training and thus improves the computational efficiency of performing optimized equipment allocation, (ii) reduce or eliminate the need for storage resources to train/generate equipment evaluation scoring machine learning models and equipment optimized allocation machine learning models and thus improves storage efficiency of performing optimized equipment allocation, and (iii) reduces or eliminates the need for transmitting extensive training data needed to generate equipment evaluation scoring machine learning models and equipment optimized allocation machine learning models and thus improves transmission/network efficiency of performing optimal equipment allocation. Via the noted advantages, various embodiments of the present invention make substantial technical contributions to the fields of equipment allocation in particular and healthcare-related predictive data analysis in general.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
   receiving, by one or more processors, one or more equipment history events for an equipment item for a demand point within a physical environment;
   inputting, by the one or more processors, the one or more equipment history events to a first neural network, causing the first neural network to determine and apply weights to the one or more equipment history events to generate a predicted evaluation score set, wherein:
   (i) the predicted evaluation score set includes a per-category predicted evaluation score for the equipment item and a risk category that relates to a particular health condition of a monitored entity that is different than the equipment item, and
   (ii) the per-category predicted evaluation score provides a predicted likelihood that an equipment associated with the equipment item is capable of transmitting a pathogen associated with the particular health condition to another equipment or another entity;
   inputting, by the one or more processors, the predicted evaluation score set to a second neural network, causing the second neural network to generate an optimized allocation scheme for the equipment item and the demand point;
   determining, by the one or more processors and based at least in part on a sensor device associated with the equipment, an equipment location for the equipment within the physical environment;
   determining, by the one or more processors, an optimal pathway between the equipment location and the demand point within the physical environment based at least in part on the optimized allocation scheme; and
   initiating, by the one or more processors and via the optimal pathway, a transportation of the equipment between the equipment location and the demand point within the physical environment.

2. The computer-implemented method of claim 1, wherein the optimized allocation scheme comprises, for each of a plurality of demand points within the physical environment, one of a plurality of equipment items within the physical environment, wherein the plurality of demand points comprises the demand point, and wherein the plurality of equipment items comprises the equipment item.

3. The computer-implemented method of claim 1, further comprising:

determining a plurality of candidate pathways within the physical environment based at least in part on a facility map for the physical environment;

determining, a pathway exposure risk score associated with the optimal pathway based at least in part on one or more exposure points associated with the optimal pathway; and selecting the optimal pathway from the plurality of candidate pathways based at least in part on the pathway exposure risk score.

4. The computer-implemented method of claim 2, wherein generating the optimized allocation scheme using the second neural network comprises:

identifying a candidate equipment assignment, wherein the candidate equipment assignment is associated with the equipment item and the demand point;

generating a predicted recommendation score for the candidate equipment assignment; and generating the optimized allocation scheme based at least in part on the predicted recommendation score.

5. The computer-implemented method of claim 4, wherein generating the predicted recommendation score comprises:

identifying an equipment type of the equipment item;
identifying a demand type of the demand point;
identifying a demand point risk profile for the demand point; and generating the predicted recommendation score based at least in part on the equipment type, the demand type, the predicted evaluation score set for the equipment item, and the demand point risk profile.

6. The computer-implemented method of claim 1, wherein each of the one or more equipment history events for the equipment item is determined based at least in part on one or more movement events associated with the equipment item.

7. The computer-implemented method of claim 6, wherein the one or more equipment history events comprise:
one or more storage location events,
one or more patient exposure events,
one or more equipment service events,
one or more handling exposure events,
one or more equipment environment events, and
one or more accessory condition events.

8. The computer-implemented method of claim 7, wherein the first neural network comprises:
a storage location event weight for the one or more storage location events,
a patient exposure event weight for the one or more patient exposure events,
an equipment service event weight for the one or more equipment service events,
a handling exposure event weight for the one or more handling exposure events,
an equipment environment event weight for the one or more equipment environment events, and
an accessory condition event weight for the one or more accessory condition events.

9. The computer-implemented method of claim 1, further comprising:

generating a contagion proximity score for the equipment item with respect to each contagion point of one or more contagion points associated with the risk category; and generating the per-category predicted evaluation score based at least in part on the contagion proximity score.

10. A system comprising one or more processors and at least one memory storing processor executable instructions that, when executed by the one or more processors, cause the one or more processors to:

receive one or more equipment history events for an equipment item for a demand point within a physical environment;

input the one or more equipment history events to a first neural network, causing the first neural network to determine and apply weights to the one or more equipment history events to generate a predicted evaluation score set, wherein:

(i) the predicted evaluation score set includes a per-category predicted evaluation score for the equipment item and a risk category that relates to a particular health condition of a monitored entity that is different than the equipment item, and (ii) the per-category predicted evaluation score provides a predicted likelihood that an equipment associated with the equipment item is capable of transmitting a pathogen associated with the particular health condition to another equipment or another entity;

input the predicted evaluation score set to a second neural network, causing the second neural network to generate an optimized allocation scheme for the equipment item and the demand point;

determine, based at least in part on a sensor device associated with the equipment, an equipment location for the equipment within the physical environment;

determine an optimal pathway between the equipment location and the demand point within the physical environment based at least in part on the optimized allocation scheme; and initiate, via the optimal pathway, a transportation of the equipment between the equipment location and the demand point within the physical environment.

11. The system of claim 10, wherein the optimized allocation scheme comprises, for each of a plurality of demand points within the physical environment, one of a plurality of equipment items within the physical environment, wherein the plurality of demand points comprises the demand point, and wherein the plurality of equipment items comprises the equipment item.

12. The system of claim 10, wherein the one or more processors are further caused to:

determine a plurality of candidate pathways within the physical environment based at least in part on a facility map for the physical environment;

determine a pathway exposure risk score associated with the optimal pathway based at least in part on one or more exposure points associated with the optimal pathway; and select the optimal pathway from the plurality of candidate pathways based at least in part on the pathway exposure risk score.

13. The system of claim 11, wherein, to generate the optimized allocation scheme using the second neural network, the one or more processors are further caused to:

identify a candidate equipment assignment, wherein the candidate equipment assignment is associated with the equipment item and the demand point;

generate a predicted recommendation score for the candidate equipment assignment; and generate the optimized allocation scheme based at least in part on the predicted recommendation score.

14. The system of claim 13, wherein, to generate the predicted recommendation score, the one or more processors are further caused to:
- identify an equipment type of the equipment item;
- identify a demand type of the demand point;
- identify a demand point risk profile for the demand point; and
- generate the predicted recommendation score based at least in part on the equipment type, the demand type, the predicted evaluation score set for the equipment item, and the demand point risk profile.

15. The system of claim 10, wherein each of the one or more equipment history events for the equipment item is determined based at least in part on one or more movement events associated with the equipment item.

16. The system of claim 10, wherein the one or more equipment history events comprise:
- one or more storage location events,
- one or more patient exposure events,
- one or more equipment service events,
- one or more handling exposure events,
- one or more equipment environment events, and
- one or more accessory condition events.

17. The system of claim 16, wherein the first neural network comprises:
- a storage location event weight for the one or more storage location events,
- a patient exposure event weight for the one or more patient exposure events,
- an equipment service event weight for the one or more equipment service events,
- a handling exposure event weight for the one or more handling exposure events,
- an equipment environment event weight for the one or more equipment environment events, and
- an accessory condition event weight for the one or more accessory condition events.

18. The system of claim 10, wherein the one or more processors are further caused to:
- generate a contagion proximity score for the equipment item with respect to each contagion point of one or more contagion points associated with the risk category; and
- generate the per-category predicted evaluation score based at least in part on the contagion proximity score.

19. One or more non-transitory computer-readable storage media including instructions that, when executed by one or more processors, cause the one or more processors to:
- receive one or more equipment history events for an equipment item for a demand point within a physical environment;
- input the one or more equipment history events to a first neural network, causing the first neural network to determine and apply weights to the one or more equipment history events to generate a predicted evaluation score set, wherein:
  - (i) the predicted evaluation score set includes a per-category predicted evaluation score for the equipment item and a risk category that relates to a particular health condition of a monitored entity that is different than the equipment item, and
  - (ii) the per-category predicted evaluation score provides a predicted likelihood that an equipment associated with the equipment item is capable of transmitting a pathogen associated with the particular health condition to another equipment or another entity;
- input the predicted evaluation score set to a second neural network, causing the second neural network to generate an optimized allocation scheme for the equipment item and the demand point;
- determine, based at least in part on a sensor device associated with the equipment, an equipment location for the equipment within the physical environment;
- determine an optimal pathway between the equipment location and the demand point within the physical environment based at least in part on the optimized allocation scheme; and
- initiate, via the optimal pathway, a transportation of the equipment between the equipment location and the demand point within the physical environment.

20. The one or more non-transitory computer-readable storage media of claim 19, wherein the optimized allocation scheme comprises, for each of a plurality of demand points within the physical environment, one of a plurality of equipment items within the physical environment, wherein the plurality of demand points comprises the demand point, and wherein the plurality of equipment items comprises the equipment item.

* * * * *

UNITED STATES PATENT AND TRADEMARK OFFICE
CERTIFICATE OF CORRECTION

PATENT NO. : 12,260,356 B2
APPLICATION NO. : 17/470551
DATED : March 25, 2025
INVENTOR(S) : Jon Kevin Muse et al.

It is certified that error appears in the above-identified patent and that said Letters Patent is hereby corrected as shown below:

In the Claims

In Column 31, Line 4, Claim 3, delete "determining," and insert -- determining --, therefor.

Signed and Sealed this
Eighth Day of July, 2025

Coke Morgan Stewart
*Acting Director of the United States Patent and Trademark Office*